United States Patent [19]

Gil

[11] Patent Number: 4,994,648

[45] Date of Patent: Feb. 19, 1991

[54] DEVICE FOR SUPPORTING A USER'S LEG

[76] Inventor: Yamila Gil, 13700 SW. 18th Ter., Miami, Fla. 33175

[21] Appl. No.: 390,275

[22] Filed: Aug. 7, 1989

[51] Int. Cl.$^5$ .................. A61H 33/00; A61F 7/00
[52] U.S. Cl. ................... 219/217; 219/521; 4/622; 128/370; 128/400
[58] Field of Search ............... 219/217, 521; 128/368, 128/370, 382, 399, 400; 248/140, 141, 142, 397, 423; 132/73, 73.5, 75; 4/621, 622; 606/27

[56] References Cited

U.S. PATENT DOCUMENTS

| D. 262,911 | 2/1982 | Weddell | 248/397 |
|---|---|---|---|
| 1,345,568 | 7/1970 | Ward | 4/622 |
| 2,050,420 | 8/1936 | Brobst | 248/423 |
| 2,119,325 | 5/1936 | Goodhart | |
| 2,630,288 | 3/1953 | Eubanks | |
| 2,676,597 | 4/1954 | Colbert | 132/73 |
| 2,836,225 | 5/1958 | Swenson | 248/397 |
| 2,838,097 | 6/1958 | Gleitsman | 248/397 |
| 3,124,328 | 3/1964 | Kortsch | |
| 3,358,951 | 12/1967 | Carter | 248/423 |
| 3,715,995 | 2/1973 | Thomas | 248/423 |
| 4,075,457 | 2/1978 | Williams | 128/370 |

FOREIGN PATENT DOCUMENTS

| 427039 | 3/1926 | Fed. Rep. of Germany | 219/217 |
|---|---|---|---|
| 2346510 | 3/1975 | Fed. Rep. of Germany | 132/73 |

Primary Examiner—Teresa J. Walberg
Attorney, Agent, or Firm—Terry M. Gernstein

[57] ABSTRACT

A device which supports a user's leg during treatment of the user's foot or leg includes a base and a pedestal assembly which support a channel-like element. The pedestal assembly and the channel-like element are adjustable for height and for angular orientation so the elements of the device are oriented and positioned to be most comfortable for each patient. Two liquid-accommodating containers are mounted in the top surface of the base, with one container on either side of the pedestal.

1 Claim, 1 Drawing Sheet

DEVICE FOR SUPPORTING A USER'S LEG

TECHNICAL FIELD OF THE INVENTION

The present invention relates to the art of supports, and to the particular field of leg supports.

BACKGROUND OF THE INVENTION

There are numerous procedures carried out on a person's feet and legs, such as podiatry, and the like in which the patient remains in a sitting position and has their foot and leg elevated during the procedure. Such position occurs during a pedicure as well.

The inventor has found that the patient who must remain seated for great lengths of time with their leg elevated and held in a raised position is subject to great discomfort. If the leg is supported by the person carrying out the procedure, both the patient and the person carrying out the procedure are subject to fatigue and discomfort.

In many procedures, both of the patient's feet will be treated, and thus, one foot can be prepared while the other is being treated. For example, in a pedicure, one foot will be soaked while the other foot is being worked on, and then the treated foot will be soaked while the other foot is treated.

While there are devices which can support a patient's leg during a period of convalescence or the like, such devices are not suitable for carrying out a procedure which requires one foot to be prepared while the other foot is treated. Thus, such devices are deficient as applied to an overall procedure.

Accordingly, there is a need for a device for supporting a patient's leg during a procedure in which one foot is treated while the other foot is being prepared for treatment and then the position of the feet is reversed.

OBJECTS OF THE INVENTION

It is a main object of the present invention to provide a device for supporting a patient's leg during a procedure in which one foot is treated while the other foot is being prepared for treatment and then the position of the feet is reversed.

It is another object of the present invention to provide a device for supporting a patient's leg during a procedure, such as a pedicure, in which one foot is treated while the other foot is being prepared for treatment and then the position of the feet is reversed.

SUMMARY OF THE INVENTION

These, and other, objects are achieved by a device that adjustably supports a patient's leg and includes liquid-accommodating containers adjacent to the leg supporting element.

Using such a device, the patient can soak one foot while the other foot undergoes treatment, then soak the treated foot while the first-mentioned foot is treated. The device can be adjusted in several planes so the patient has their leg and foot supported in a position that is most comfortable for that particular patient.

DESCRIPTION OF THE DRAWING FIGURES

DETAILED DESCRIPTION OF THE PREFERRED EMBODIMENT OF THE INVENTION

Figure 1:
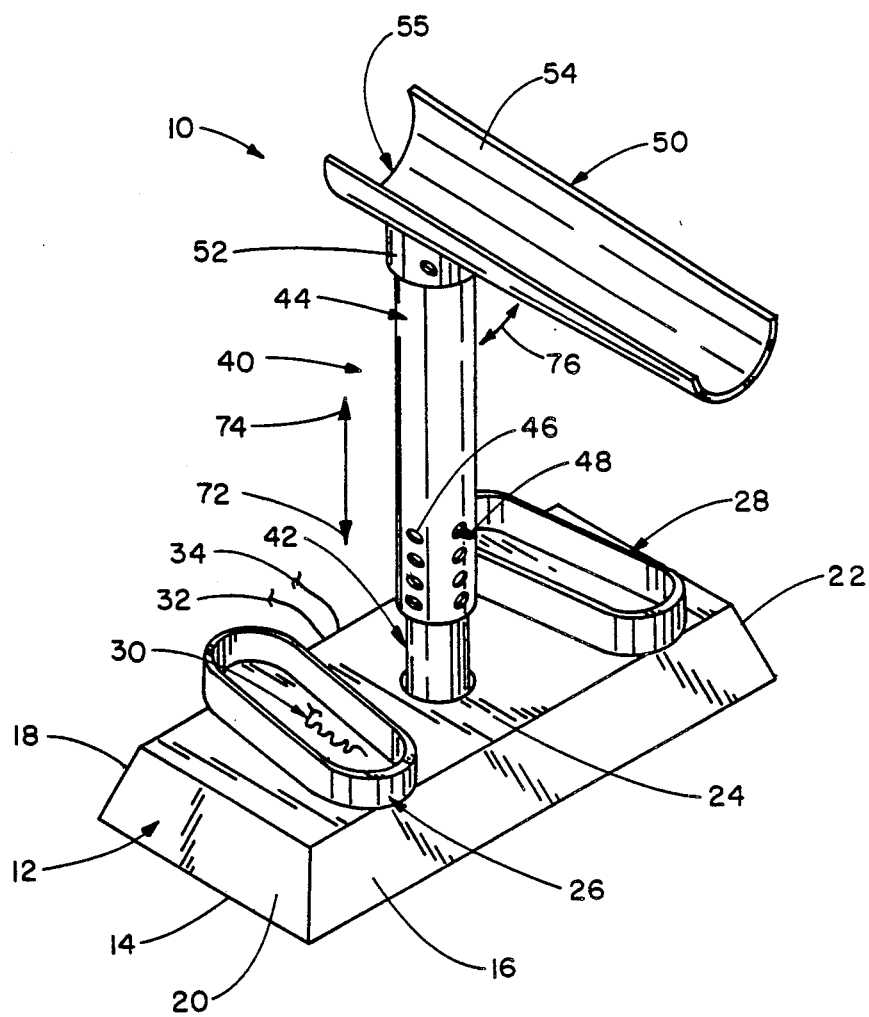
FIG. 1 is a perspective view of the device embodying the present invention.

Shown in FIG. 1 is a device 10 for supporting a patient's leg and foot in an elevated position so that such foot can undergo treatment, while the other foot is being soaked in preparation for such treatment.

The device 10 includes a base 12 which has a bottom 14 that rests on a support surface, such as a floor, and sides 16 and 18, and ends 20 and 22 that converge inwardly towards each other from the bottom. The base also includes a top surface 24, and can be formed of any suitable material, such as plastic or the like.

Two liquid-accommodating containers 26 and 28 are mounted on the top surface 24 and are shaped to correspond to the shape of a foot so a patient's foot will be comfortably accommodated therein. Liquid, such as water, or the like, is located in the containers, and the device can include a heater element 30 connected to a suitable source of power, such as utility power by a cord 32 and to a switch by a cord 34 to keep the container liquid warm if necessary. Only one heater is shown, but both containers 26 and 28 can include such a heater. The heaters will be embedded in the base so that there is no danger that electricity will be applied to the patient.

The device 10 further includes a pedestal assembly 40 for elevating and supporting a patient's leg. The pedestal assembly 40 includes a pedestal element 42 fixedly mounted on the base 12 between the containers 26 and 28 to extend upwardly therefrom in the leg supporting configuration of the device 10. The pedestal element 42 is cylindrical and includes a plurality of holes that are arranged in rows that are spaced apart along the longitudinal axis of the element 42 and columns that are spaced apart around the element 42. These holes are not seen in FIG. 1 because they are hidden by tubular sleeve element 44.

The tubular sleeve 44 telescopingly receives the pedestal element 42 and includes a plurality of holes, such as hole 46, that are arranged in a plurality of columns that are spaced apart from each other around the circumference of the sleeve and a plurality of rows that are spaced apart from each other along the axis of the sleeve. The holes 46 are spaced and positioned in accordance with the spacing and positioning of the holes in the pedestal element so that such holes can be aligned to receive a bolt, such as bolt 48 which can be inserted through such aligned holes. The holes 46 are located in a proximal end of the sleeve.

The device 10 further includes a leg support assembly 50 attached to the sleeve 44 at a distal end of that sleeve. The leg support assembly includes a cap 52 that fits over the distal end of the sleeve 44 and is connected thereto as will be discussed below. A channel-like element 54 is supported at near a proximal end 55 thereof on the cap and extends away from such cap. The patient rests his leg in the channel-like element 54 with the patient's foot located near the distal end thereof.

As is often the case, a patient may be uncomfortable in one position as opposed to another, therefore, it is desirable to be able to change the position of the leg support assembly to accommodate such patient. Therefore, the device 10 can include an adjusting means 56, shown in FIG. 2. It is noted that the adjusting means 56 is not shown in FIG. 1 for the sake of clarity. The adjusting means includes a projection support 58 mounted on the cap 52 to extend upwardly from that cap in the leg supporting position of the device 10. A hinge element 60 connects the support 58 to the channel-like element 54 so that the element 54 can move in the directions indicated by the double-headed arrow 62 between the angled orientation shown in FIG. 2 to the nearly horizontal orientation shown in FIG. 1.

The adjusting means further includes an arcuate arm 64 having a plurality of holes, such as hole 66 defined therein at spaced apart locations along the length of the arm. The channel-like member 54 includes a hole (not seen) in its side that is sized to correspond to the size of the holes 66 whereby a bolt, such as bolt 68 can be fit through the holes in the arm and the channel-like member when such holes are aligned to attach the channel-like member to the arm. Several holes 66 can be used to provide a plurality of positions for the channel-like member.

Figure 2:
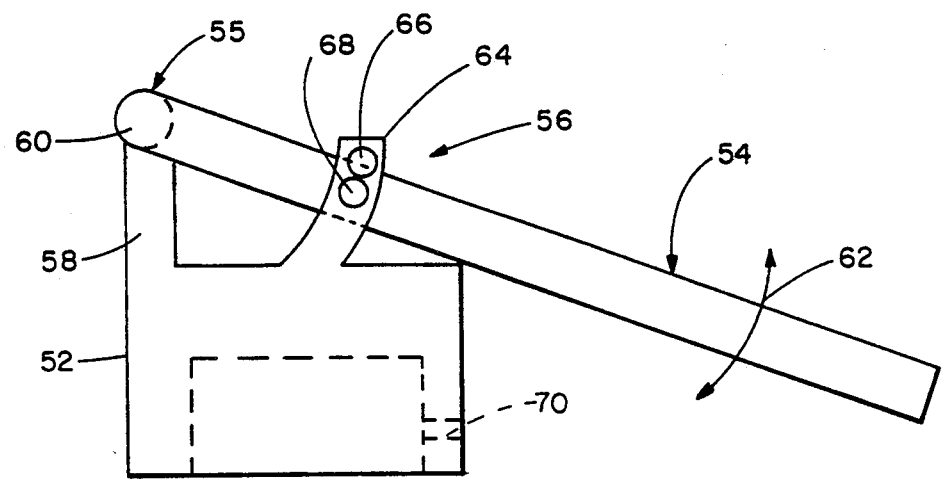
FIG. 2 is an elevational view of a position changing assembly used in the device of the present invention.

As can be seen in FIG. 2, the cap 52 includes a hole 70 that receives a bolt 19 (see FIG. 1) to connect the cap to the sleeve 44.

In use, the device 10 is set to the desired height by moving the sleeve in one of the directions indicated in FIG. 1 by the arrows 72 and 74, then is adjusted angularly as indicated by the double-headed arrow 76 by selecting the holes in the sleeve and pedestal element that provide the proper height and angle orientations and then inserting the bolt 48 through the selected holes. The channel-like element is adjusted for its horizontal orientation by selecting one of the holes 66 in the arm 64, aligning the hole in the channel-like element with such selected hole and inserting the bolt 68 through that hole and the aligned holes.

The containers 26 and 28 are filled with liquid, and heated, and the device is ready for use. The patient rests one foot in one of the containers and rests their other leg on the channel-like element for treatment. After the treatment is completed, the treated foot is placed in the other container, and the soaked foot is moved onto the channel-like element.

It is understood that while certain forms of the present invention have been illustrated and described herein, it is not to be limited to the specific forms or arrangements of parts described and shown.

I claim:

1. A device for supporting a user's leg during a pedicure comprising:
   (A) a base having a top surface;
   (B) two liquid-accommodating containers mounted on said top surface;
   (C) a pedestal assembly mounted on said base between said liquid-accommodating containers and including
     (1) a cylindrical pedestal element mounted on said base and having a plurality of pedestal holes defined therein to be arranged in rows that are spaced apart along the length of said cylindrical pedestal element and columns that are spaced apart around the circumference of said cylindrical pedestal element,
     (2) a tubular sleeve telescopingly receiving said pedestal element and including a plurality of sleeve holes defined therein to be arranged in rows that are spaced apart along the length of said tubular sleeve and columns that are spaced apart around the circumference of said tubular sleeve, and
     (3) a first bolt which is sized to fit through said pedestal holes and through said sleeve holes to attach said sleeve to said pedestal element when said pedestal and sleeve holes are aligned;
   (D) a leg support assembly attached to said sleeve and including
     (1) a cap which receives said sleeve, and
     (2) a channel-like element attached at a rear end thereof to said cap to extend away from said cap and for supporting a use's leg;
   (E) an angle adjusting means on said cap, said angle adjusting means including
     (1) an upstanding arm connected at one end thereof to said cap, and having a second end spaced from said cap,
     (2) a hinge element on said upstanding arm second end and being connected to said channel-like member rear end and connecting said channel-like member to said cap,
     (3) an elongate arcuate arm mounted on said cap and having a plurality of arm holes defined therein at positions which are spaced apart from each other along a length dimension of said elongate arcuate arm,
     (4) a bolt-receiving hole defined in said channel-like element near said channel-like member rear end,
     (5) a second bolt sized to be received through said channel-like element holes and said arm holes to couple said arm to said channel-like element,
     (6) a cap hole in said cap and a top hole defined in said sleeve and a third bolt which is inserted through said cap hole and said sleeve top hole,
     (7) one of said arcuate arm holes being defined to cooperate with one of said channel-like member holes to position said channel-like member in contact with said cap when said second bolt is received through said co-operating holes; and
   (F) a heater unit in at least one of said liquid-accommodating containers.

* * * * *